(12) United States Patent
Yarbrough et al.

(10) Patent No.: US 10,288,543 B2
(45) Date of Patent: May 14, 2019

(54) METHODS FOR DETERMINING MOISTURE PERMEABILITY IN TEXTILES

(71) Applicant: COLUMBIA INSURANCE COMPANY, Omaha, NE (US)

(72) Inventors: Chris W. Yarbrough, Dalton, GA (US); Alan Buttenhoff, Tunnel Hill, GA (US)

(73) Assignee: COLUMBIA INSURANCE COMPANY, Omaha, NE (US)

( * ) Notice: Subject to any disclaimer, the term of this patent is extended or adjusted under 35 U.S.C. 154(b) by 158 days.

(21) Appl. No.: 15/408,109

(22) Filed: Jan. 17, 2017

(65) Prior Publication Data
US 2017/0205327 A1 Jul. 20, 2017

Related U.S. Application Data

(60) Provisional application No. 62/279,714, filed on Jan. 16, 2016.

(51) Int. Cl.
*G01N 15/08* (2006.01)
*G01N 33/36* (2006.01)

(52) U.S. Cl.
CPC ........... *G01N 15/08* (2013.01); *G01N 33/367* (2013.01); *G01N 2015/0866* (2013.01)

(58) Field of Classification Search
CPC ...... G01N 15/08; G01N 33/36; G01N 33/367; G01N 2015/0866
See application file for complete search history.

(56) References Cited

U.S. PATENT DOCUMENTS

| | | |
|---|---|---|
| 2,993,368 A | 7/1961 | Schlein |
| 3,254,526 A | 6/1966 | Yarbrough |
| 3,323,349 A | 6/1967 | Savage et al. |
| 3,364,726 A | 1/1968 | Bonham |
| 3,835,697 A | 9/1974 | Schneider et al. |
| 4,055,984 A | 11/1977 | Marx |
| 4,194,041 A | 3/1980 | Gore et al. |

(Continued)

FOREIGN PATENT DOCUMENTS

| | | | |
|---|---|---|---|
| CN | 203688525 U * | 7/2014 | ............. G01N 15/08 |
| DE | 202009001801 U1 | 5/2009 | |

(Continued)

OTHER PUBLICATIONS

U.S. Appl. No. 62/279,714, filed Jan. 16, 2016, Chris W. Yarbrough.

*Primary Examiner* — Nguyen Q. Ha
(74) *Attorney, Agent, or Firm* — Ballard Spahr LLP

(57) ABSTRACT

Disclosed is a method for determining moisture permeability of a textile. The method includes: a) providing at least one textile sample having a top surface and an opposed bottom surface, wherein at least a portion of the top surface is configured into a bowl shape for receiving a predetermined amount of a test liquid; b) introducing the predetermined amount of the test liquid into the bowl shape sample such that there is a minimum depth of the liquid contained above at least a portion of the top surface; and c) after a predetermined period of time, determining the moisture permeability of the textile sample by analyzing liquid penetration characteristics of any of the test liquid that may have permeated through the textile.

18 Claims, 1 Drawing Sheet

(56) References Cited

U.S. PATENT DOCUMENTS

| | | |
|---|---|---|
| 4,613,544 A | 9/1986 | Burleigh |
| 4,619,853 A | 10/1986 | Blyth et al. |
| 5,171,877 A | 12/1992 | Knaup et al. |
| 5,348,785 A | 9/1994 | Vinod |
| 5,390,531 A | 2/1995 | Taylor |
| 5,493,899 A | 2/1996 | Beck et al. |
| 5,558,916 A | 9/1996 | Heim et al. |
| 5,563,329 A | 10/1996 | Smith et al. |
| 5,612,113 A | 3/1997 | Irwin, Sr. |
| 5,763,040 A | 6/1998 | Murphy et al. |
| 5,887,477 A | 3/1999 | Newman |
| 6,253,526 B1 | 7/2001 | Murphy et al. |
| 6,430,989 B1 | 8/2002 | Van Dyke et al. |
| 6,794,010 B1 | 9/2004 | Yamaguchi et al. |
| 6,802,870 B2 | 10/2004 | Chang et al. |
| 6,824,854 B2 | 11/2004 | Materniak et al. |
| 6,872,445 B2 | 3/2005 | Vinod |
| 6,895,811 B2 | 5/2005 | Carey et al. |
| 6,939,580 B2 | 9/2005 | Enomoto et al. |
| 7,131,316 B2 | 11/2006 | Doehla et al. |
| 7,157,121 B2 | 1/2007 | Jones, Jr. |
| 7,226,877 B2 | 6/2007 | Bascom et al. |
| 8,266,956 B2 | 9/2012 | Weaver et al. |
| 2005/0118913 A1 | 6/2005 | Jen |
| 2006/0251853 A1 | 11/2006 | Ingram |
| 2017/0030010 A1* | 2/2017 | Baumann ............ D06M 15/263 |

FOREIGN PATENT DOCUMENTS

| | | | |
|---|---|---|---|
| EP | 0804645 A1 | 11/1997 | |
| EP | 1435518 A2 | 7/2004 | |
| GB | 1180960 A * | 2/1970 | ............ A61F 5/485 |
| WO | WO-00/09798 A1 | 2/2000 | |
| WO | WO-01/75215 A1 | 10/2001 | |
| WO | WO-2008/144635 A1 | 11/2008 | |

\* cited by examiner

METHODS FOR DETERMINING MOISTURE PERMEABILITY IN TEXTILES

CROSS-REFERENCE TO RELATED APPLICATIONS

This application claims priority to and the benefit of U.S. Provisional Patent Application Ser. No. 62/279,714, filed Jan. 16, 2016, which application is hereby incorporated by reference herein in its entirety.

FIELD

Disclosed herein are methods for determining moisture permeability of textiles, in, such as, for example and without limitation, carpets and carpet products.

BACKGROUND

Textiles are flexible materials made of a network of natural or artificial fibers, such as yarn or thread. Textiles are generally formed by weaving, knitting, tufting, knotting, or felting the fibers. For example, carpets, a type of textile, are generally produced by tufting carpet yarns into and through a primary backing, which is comprised of a woven or non-woven material or a combination of such materials. It is common in the carpet industry to also apply a secondary backing that can include jute or other woven material. In some aspects, the secondary backings can include a foam material, which can also act as the cushion for the carpet.

When a liquid such as a beverage, wine, or the like, spills onto the surface of the textile, the liquid can flow through the material to the back of the textile and soaks completely through the textile, contaminating the underlying surfaces. Moisture permeability or degree of fluid penetration of textiles is a top concern in a number of textile applications. For example, moisture permeability or fluid penetration of carpets is an important consideration for anyone who keeps a dog or a cat as a pet, or in healthcare facilities where penetrations of blood, urine or other bodily fluids into and through a carpet are problems. While it is universally recommended by the carpet manufacturers to clean up spills promptly, it is also generally recognized that it is highly impracticable to clean and absorb the spills before at least some of the fluid has penetrated though the backing to the sub-floor. This often leads to permanent odors, stains, formation and entrapment of bacteria, or other carpet damaging or destroying problems.

There are existing methodologies for analyzing permeability of textile materials, such as carpets. For example, the British Spill test is the National Health Service Patient Area Requirement for the United Kingdom, Method E: Part 2. This test involves the controlled spilling of a blue dyed liquid through a funnel onto a generally flat planar surface or carpet face from a 1-meter height. The liquid remains in a concentrated area for 24 hours, after which time cuts are made through the carpet in the area of the spill to establish whether there was penetration into or through the carpet composite.

It would be beneficial, however, to have improved methodologies for analysis of permeability and liquid penetration in order to have greater understanding and data on moisture permeability properties of textiles under various conditions and circumstances. This need and other needs are at least partially satisfied by the methods disclosed herein.

SUMMARY

In accordance with the purpose(s) of the disclosed methods, as embodied and broadly described herein, the invention, in one aspect, relates to a new method for determining moisture permeability of a textile. The method uses textile samples formed in the shape of bowls for liquid penetration analysis, to the point of evaporation.

The method generally comprises the steps of forming a textile sample into a liquid-receiving configuration, such as, for example and without limitation, a shape that is at least partially concave or bowl-like, the textile sample having a top surface and an opposed bottom surface such that at least a portion of the top surface of the textile is configured as a receptacle for receiving a predetermined amount of a test liquid. A predetermined amount of test liquid is then introduced into the bowl-shaped textile receptacle such that there is a minimum depth of the liquid retained above at least a portion of the top surface of the textile. The test liquid, or at least a portion thereof depending upon the permeability of the textile sample, is allowed to remain in the bowl-shaped receptacle for a predetermined period of time. During and after this predetermined period of time, various characteristics of moisture permeability of the textile sample can be determined, measured, and analyzed. For example, it is contemplated that moisture permeability can be determined at least in part by the penetration of the test liquid through the textile sample (from the top surface to the bottom surface of the textile sample).

Additional aspects of the invention will be set forth, in part, in the detailed description, and claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF THE FIGURES

These and other features of the invention will become more apparent in the detailed description in which reference is made to the appended drawings wherein.

DETAILED DESCRIPTION

Figure 1:
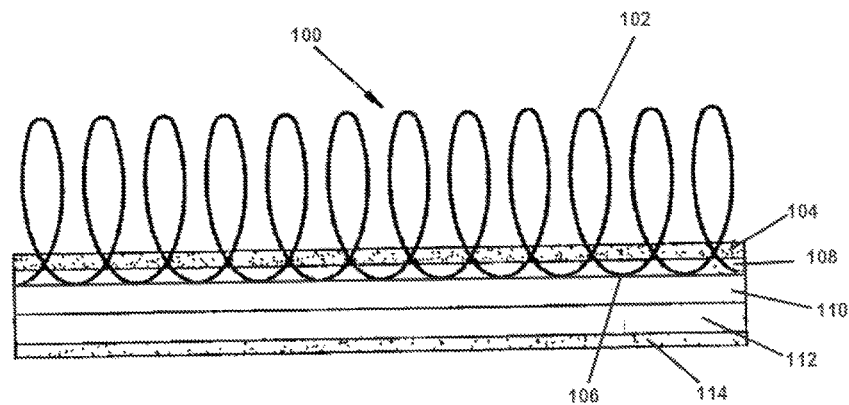
FIG. 1 depicts an exemplary structure of a textile sample such as a carpet tile as disclosed herein.

The present invention can be understood more readily by reference to the following detailed description, examples, drawings, and claims, and their previous and following description. However, before the present compositions, articles, devices, systems, and/or methods are disclosed and described, it is to be understood that this invention is not limited to the specific compositions, articles, devices, systems, and/or methods disclosed unless otherwise specified, as such can, of course, vary. It is also to be understood that the terminology used herein is for the purpose of describing particular aspects only and is not intended to be limiting.

The following description of the invention is also provided as an enabling teaching of the invention in its best, currently known aspect. To this end, those of ordinary skill in the relevant art will recognize and appreciate that changes and modifications can be made to the various aspects of the invention described herein, while still obtaining the beneficial results of the present invention. It will also be apparent that some of the desired benefits of the present invention can be obtained by selecting some of the features of the present invention without utilizing other features. Accordingly, those of ordinary skill in the relevant art will recognize that many modifications and adaptations to the present invention are possible and can even be desirable in certain circumstances and are thus also a part of the present invention. Thus, the following description is provided as illustrative of the principles of the present invention and not in limitation thereof.

Various combinations of elements of this disclosure are encompassed by this invention, e.g. combinations of elements from dependent claims that depend upon the same independent claim.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

All publications mentioned herein are incorporated herein by reference to disclose and describe the methods and/or materials in connection with which the publications are cited.

It is also to be understood that the terminology used herein is for the purpose of describing particular aspects only and is not intended to be limiting. As used in the specification and in the claims, the term "comprising" may include the aspects "consisting of" and "consisting essentially of" Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used herein, the singular forms "a," "an" and "the" include plural referents unless the context clearly dictates otherwise. Thus, for example, reference to a "textile" includes aspects having two or more textiles unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" mean that the subsequently described event or circumstance may or may not occur, and that the description includes instances where said event or circumstance occurs and instances where it does not.

As used herein, "textile" is used in the manner as would be recognized by one of ordinary skill in the art. For example, textiles generally comprise flexible materials made of a network or plurality of natural or artificial fibers, such as yarn or thread.

As used herein, "carpet" is used in the manner as would be recognized by one of ordinary skill in the art. The definition of carpet herein does not include products that would be known to one of ordinary skill in the art as "resilient flooring." As an example, products that fall under the category of resilient flooring include, but are not limited to, linoleum, vinyl tiles, cork tiles, rubber tiles and floor mats.

As used herein, and unless the context clearly indicates otherwise, the term carpet is used to generically include carpet tiles, broadloom carpets and area rugs. To that end, "broadloom carpet" means a broadloom textile flooring product manufactured for and intended to be used in roll form.

As used herein, "spillage" is used in the manner as would be recognized by one of ordinary skill in the art. For example, spillage can include liquid that may penetrate or leak through the textile sample while the textile sample is in the liquid-receiving configuration.

The term "fiber" as used herein includes fibers of extreme or indefinite length (i.e. filaments) and fibers of short length (i.e., staple fibers).

The term "yarn" as used herein refers to a continuous strand or bundle of fibers.

References in the specification and concluding claims to parts by weight of a particular element or component in a composition or article, denotes the weight relationship between the element or component and any other elements or components in the composition or article for which a part by weight is expressed. Thus, in a composition or a selected portion of a composition containing 2 parts by weight of component X and 5 parts by weight component Y, X and Y are present at a weight ratio of 2:5, and are present in such ratio regardless of whether additional components are contained in the composition.

A weight percent of a component, or weight %, or wt. %, unless specifically stated to the contrary, is based on the total weight of the formulation or composition in which the component is included.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Methods

Figure 2:
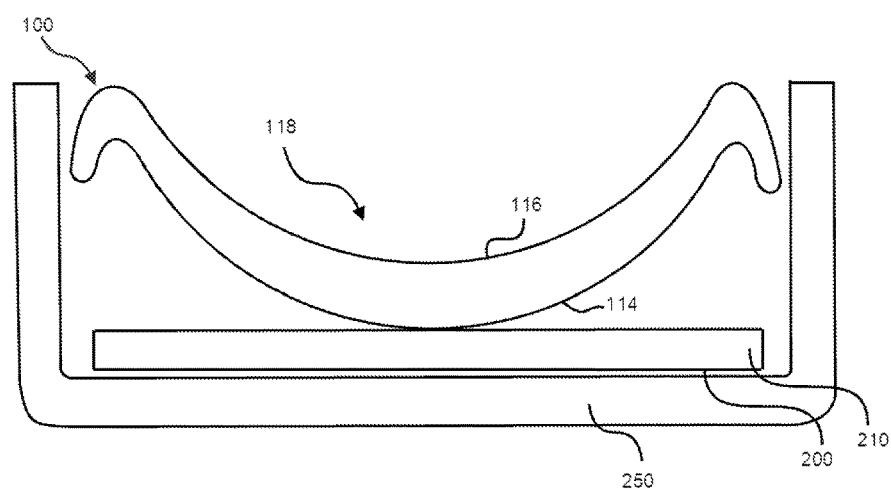
FIG. 2 is a cross-sectional schematic view of an exemplary textile sample deformed to a liquid-receiving configuration and held in operable position for testing of the textile sample for moisture permeability.

In various aspects, and with reference to FIGS. 1 and 2, described herein are methods for determining or analyzing the moisture (e.g., liquid) permeability of textiles. In one aspect, the method for determining moisture permeability of a textile 100, comprises: a) positioning at least one textile sample 100 in a liquid-receiving configuration, the at least one textile sample 100 having a top surface 116 and an opposed bottom surface 114, wherein, in the liquid-receiving configuration, at least a portion of the top surface 116 of the at least one textile sample 100 is configured in a non planar arrangement such that it is configured for receiving and retaining a predetermined amount of a liquid; b) introducing the predetermined amount of the liquid onto the top surface 116 of the at least one textile sample 100 such that there is a minimum depth of the liquid contained above at least a portion of the top surface 116. In this aspect, at least a portion of the top surface 116 of the at least one textile sample 100 can be deformed to have a concave profile defining a testing site 118 that is configured to receive the liquid. Optionally, the at least one textile sample 100 can comprise a single textile sample that is deformed to have a concave profile and testing site as disclosed herein. Alternatively, in other aspects, it is contemplated that the at least one textile sample 100 can comprise a plurality of textile samples that cooperate to define a concave profile and testing site as disclosed herein. In these aspects, it is contemplated that the plurality of textile samples can be coupled or secured together before the concave profile and testing site are produced.

To form the concave profile, it is contemplated that the at least one textile sample 100 can be secured in an operable position (optionally, by at least one clamp, clip or the like (not shown)). For example, the at least one textile sample 100 can comprise a center portion where the testing site 118 is located and outer portions (e.g., corners or edges) surrounding the center portion that are detachably secured together to form the concave profile (e.g, an indentation or recessed portion) configured to receive the liquid and then subsequently maintain the liquid-receiving configuration. Optionally, the outer portions of the at least one textile sample 100 can be secured together with at least one clamp, clip, or the like. In another example, at least a portion of the at least one textile sample 100 can be positioned within a mold that is configured to produce a concave profile within the at least one textile sample when a center portion of the at least one textile sample is deformed such that the bottom surface 114 of the at least one textile sample contacts the inner surfaces of the mold. With the center portion of the at least one textile sample deformed to have a shape corresponding to the shape of the mold, the outer portions of the at least one textile sample that extend outside the mold can be secured (e.g., clamped) to one another or to a support structure (e.g., a portion of the mold or a portion of a container as disclosed herein). In one exemplary aspect, it is contemplated that the mold can define a central bore that extends completely through the mold such that the mold can receive liquid that penetrates through the at least one textile sample, thereby allowing the at least one textile sample to remain secured to or otherwise engaged with the mold throughout the methods disclosed herein. While in the liquid-receiving configuration, the test liquid, or at least a portion thereof depending upon the permeability of the sample, can be retained by or allowed to remain within the textile sample 100 for a predetermined period depending on the permeability characteristics to be analyzed. Thus, after the test liquid has been introduced and retained, the moisture permeability of the textile sample can be determined. In this context, the term "retained" indicates that the test liquid is allowed to remain within the textile sample and is not actively removed from the testing site 118; rather, the test liquid is allowed to freely remain within the testing site (i.e., receptacle) or to penetrate through the textile sample.

In various aspects, the at least one textile sample can be any textile 100 as is known in the art. In a further aspect, the textile can comprise any material which comprises a network or plurality of fibers 102. In a still further aspect, the fibers 102 can comprise yarn or thread. In a yet further aspect, the fibers can be natural or synthetic fibers. In an even further aspect, the plurality of fibers 102 can comprise synthetic fibers, natural fibers, polyesters, polyamides, acrylics, rayon, cellulose acetate, cotton, wool, or any combination thereof.

In some aspects, the textile 100 can comprise a carpet or greige good. In a further aspect, as shown in FIG. 1, the carpet 100 can be constructed with a primary backing material 104 and includes tufted carpet and non-tufted carpet such as needle punched carpet. To form the tufted carpet, yarn is tufted through the primary backing material 104 such that the longer length of each tuft or stitch extends through the face surface of the primary backing material 104.

In some aspects, the plurality of fibers 102 of the carpet 100 or greige good can be provided as at least one yarn (a single yarn or a plurality of yarns). In other aspects, the plurality of fibers 102 can be provided independently as separate fibers. In some aspects, the plurality of fibers 102 form tufts. In some aspects, a portion of the plurality of the fibers 102 is exposed at the back surface of the primary backing 104. Optionally, in these aspects, a portion of the plurality of the fibers 102 is exposed or extends downwardly from the back surface of the primary backing to form back stitches 106.

In one aspect, as also shown in FIG. 1, the carpet 100 or greige good can further comprise a precoat layer 108 disposed between the back surface of the primary backing 104 and any subsequent backing layers, such as an adhesive backing composition 110 or a secondary backing layer 112. The precoat layer 108 can be applied to the backside of the primary backing layer 104, followed by the adhesive composition 110 being disposed adjacent to the precoat layer 108. Alternatively, if the precoat layer 108 is not present, the adhesive composition 110 can be disposed directly on the backside of the primary backing material 104. The precoat layer 108 can be used to lock the plurality of fibers 102 or tufts in place. In some aspects, the precoat layer 108 can provide additional strength to the tufts (i.e., tuft bind strength). In yet another aspect, the precoat layer 108 can be used to prevent or substantially prevent adhesive from the adhesive composition 110 from penetrating through (the openings between) the plurality of fibers (e.g., the tufts) 102 in the direction of the carpet top face.

In some aspects, the at least one textile sample 100 is a carpet or carpet tile. In additional aspects, the carpet or carpet tile comprises at least one backing layer as disclosed herein.

It should be appreciated that by analyzing a textile such as those described herein, the disclosed method can be used to assess permeability and liquid penetration of the textile as a whole or any portion or composite layer of the textile. For example, in exemplary aspects, the disclosed method can be used to analyze permeability and liquid penetration characteristics of a textile backing layer, such as a polymeric backing layer.

In further aspects, the at least one textile sample has a surface area from about 1 square inch to about 100 square feet, including exemplary surface areas of about 1, 2, 3, 4, 5, 6, 7, 8, 9, 10, or 11 square inches, or about 1, 2, 3, 4, 5, 6, 7, 8, 9, 10, 11, 15, 20, 25, 50, 75, or 95 square feet.

In some aspects and with reference to FIG. 2, at least a portion of the top surface 116 of the at least one textile sample 100 is concave or substantially concave (e.g., bowl-like) in shape. Optionally, in these aspects, at least a portion of the top surface 116 of the at least one textile sample 100 is deformed to have an arcuate cross-sectional shape. In further aspects, at least a portion of the top surface 116 of the at least one textile sample 100 is not planar or is not substantially planar in shape. In still further aspects, at least one portion of the top surface 116 of the at least one textile sample 100 is shaped to receive and hold the predetermined amount of liquid. In these aspects, at least one portion of the top surface 116 of the at least one textile sample 100 is configured to be in a liquid-receiving configuration defining a testing site 118 as further disclosed herein.

In further aspects, the testing site 118 has a surface area between about 1 square inch to about 100 square feet, including exemplary surface areas of about 1, 2, 3, 4, 5, 6, 7, 8, 9, 10, or 11 square inches, or about 1, 2, 3, 4, 5, 6, 7, 8, 9, 10, 11, 15, 20, 25, 50, 75, or 95 square feet. In still further aspects, the bowl-shaped portion of the at least one textile sample can define a testing site 118.

In some aspects, the bowl-shaped portion of the at least one textile sample 100 has a surface area between about 1 square inch to about 100 square feet, including exemplary surface areas of about 1, 2, 3, 4, 5, 6, 7, 8, 9, 10, or 11 square inches, or about 1, 2, 3, 4, 5, 6, 7, 8, 9, 10, 11, 15, 20, 25, 50, 75, or 95 square feet. In further aspects, while in the liquid-receiving configuration, the bowl-shaped portion of the at least one textile sample 100 can have a vertical depth of between about 1 millimeter (mm) to about 300 mm, including exemplary depths of about 1, 2, 3, 4, 5, 6, 7, 8, 9, 10, 11, 15, 20, 25, 30, 35, 40, 45, 50, 55, 60, 75, 100, 200, or 300 mm.

In various aspects, the test liquid can be any desired liquid for which permeability data is desired to be acquired and analyzed. For example, in some aspects, the test liquid can comprise at least one dye. An exemplary non-limiting test liquid can be a stain solution comprising an acid red/cationic blue solution, which can be formed by weighing 800+/−1 milligram (mg) of FD&C Red 40 and 2.0 grams (g) of liquid Cationic Blue Dye or 800+/−1 mg of Cationic Blue Dye Power and then mixing both in 4 liters (L) of deionized water at 23.9+/−5.6° C. (75+/−10° F.). Alternatively, another exemplary stain solution can be a methylene blue solution, which can be formed by using a 0.1% solution of Methylene Blue aqueous solution available from either Fisher or VWR (the 1.0% solution can be diluted 1:10 for the same effect).

In further aspects, the test liquid can comprise carbonated and non-carbonated beverages, juices, milk, coffee, tea, wine, or any other liquid substances known to impart stains, such as and without limitation, human or pet body fluids, food fluids, food processing fluids, rain, or combinations thereof. In further aspects, the predetermined amount of test liquid used in the disclosed method can depend, in part, on the size of the test sample. For example, the amount of test liquid can be at least 1 milliliter (ml), including exemplary volumes of about 1, 2, 3, 4, 5, 6, 7, 8, 9, 10, 11, 15, 20, 25, 50, 75, or 95 ml, or about 1, 2, 3, 4, 5, 6, 7, 8, 9, 10, 11, 12, or 20 ounces. In yet further aspects, the test liquid can be introduced into the bowl-shaped portion of the textile sample through an apparatus having a hollow channel disposed therein, such as for example, a funnel.

In some aspects, as shown in FIG. 2, the at least one textile sample 100 is positioned on top of or in a support apparatus 200. In further aspects, the support apparatus 200 can comprise a mesh apparatus 210, such as a metal mesh apparatus as is known in the art. In still further aspects, the metal mesh apparatus 210 can be further positioned inside a larger container 250 intended to retain any liquid that penetrates through the sample. Optionally, it is contemplated that the volume of liquid collected within the larger container 250 can be used to assess performance of the at least one textile sample 100.

In various aspects, the at least one textile sample 100 can be tested for any desired time and intervals. In further aspects, the at least one textile sample 100 is tested for at least 1 second, 1 minute, 3 minutes, 5 minutes, 10 minutes, 15 minutes, 20 minutes, 30 minutes, 1 hour, 2 hours, 3 hours, 4 hours, 5 hours 6, hours, 12 hours, 1 day, 2 days, or 1 week. In still further aspects, the at least one textile sample 100 is tested for spillage (e.g., penetration) and movement of the at least one textile sample is minimized (or, optionally, the at least one textile sample is held stationary) for at least 24 hours. In yet further aspects, the at least one textile sample 100 is tested for spillage (e.g., penetration), and movement of the at least one textile sample 100 is optionally held stationary for at least 1 hour. In yet further aspects, the at least one textile sample 100 is tested for spillage (e.g., penetration) and wetness, and movement of the at least one textile sample 100 is minimized for at least 3 minutes. In further aspects, the sample can be evaluated for any period of time sufficient for substantially complete evaporation of the test liquid.

Alternatively, in some optional aspects, the at least one textile sample 100 is placed onto a flat surface for at least 24 hours. In some aspects, the at least one textile sample 100 is not disturbed (i.e., held stationary). In other aspects, a non-wicking material or media is positioned between the at least one textile sample 100 and the flat surface. In a further aspect, the non-wicking material or media is paper, such as butcher paper.

In further aspects, determining the moisture permeability of the textile sample 100 can occur at any desired interval or time after introducing the predetermined amount of liquid onto the top surface of the at least one textile sample, including exemplary intervals of 1 second, 30 seconds, 1 minute, 2 minutes, 3 minutes, 4 minutes, 5 minutes, 6 minutes, 7 minutes, 8 minutes, 9 minutes, 10 minutes, 15 minutes, 20 minutes, 30 minutes, 1 hour, 1 day, or 1 week. In some aspects, determining the moisture permeability of the textile sample occurs at least 3 minutes after introducing the predetermined amount of liquid onto the top surface 116 of the at least one textile sample 100. In other aspects, determining the moisture permeability of the textile sample 100 occurs at least 1 hour after introducing the predetermined amount of liquid onto the top surface 116 of the at least one textile sample 100. In other aspects, determining the moisture permeability of the textile sample occurs at least 24 hours after introducing the predetermined amount of liquid onto the top surface 116 of the at least one textile sample 100. In further aspects, determining the moisture permeability of the textile sample can be repeated until the at least one textile sample has reached a moisture equilibrium or until the at least one textile sample 100 is dry.

In various aspects, determining the moisture permeability of the textile sample can comprise any desired analytical method. In some aspects, determining the moisture permeability of the textile sample 100 can comprise a qualitative test, such as, for example, determining whether or not liquid is present after a predetermined period. In other aspects, determining the moisture permeability of the textile sample 100 can comprise a quantitative test, such as for example, an amount of liquid present after a predetermined period. In further aspects, the scale and threshold for determining penetration can be any desired amount or level of penetration.

For example, in some aspects, when an amount of a liquid is introduced (e.g., spilled) on the testing site 118 of the sample 100 to evaluate the permeability of the sample, the liquid remains substantially contained within the point of contact of the liquid and the carpet.

In other aspects, when an amount of a liquid is introduced (e.g., spilled) on the testing site 118 of the sample 100 to evaluate the permeability of the sample, an area of a spill can be measured from the time of the spill to a 24 hour test period, or the like. For example, at the end of the test period, a spill spot or a spill area can be contained within about 10% of an original spill spot or area, about 9% of an original spill spot or area, about 8% of an original spill spot or area, about 7% of an original spill spot or area, about 6% of an original spill spot or area, about 5% of an original spill spot or area, about 4% of an original spill spot or area, about 3% of an original spill spot or area, about 2% of an original spill spot or area, about 1% of an original spill spot or area, about 0.5% of an original spill spot or area, about 0.1% of an original spill spot or area, or about 0.01% of an original spill spot or area.

In various aspects, determining the moisture permeability of the textile sample 100 can comprise determining the presence of liquid onto the top or bottom surface 116, 114 of the at least one textile sample 100. In some aspects, the presence of liquid onto the top surface 116 of the at least one textile sample 100 is determined by touching the top surface of the at least one textile sample. In other aspects, the presence of liquid onto the bottom surface 114 of the at least one textile sample 100 is determined by touching the bottom surface of the at least one textile sample.

In various aspects, determining the moisture permeability of the textile sample 100 can comprise determining the presence or penetration of liquid onto a non-wicking material or media located below the sample. In still further aspects, penetration of the liquid onto the bottom surface of the at least one textile sample can be determined by assessing the non-wicking material for a stain. In yet further aspects, determining the moisture permeability of the textile sample can comprise determining the number and size of at least one stain. For example, in one aspect, if no stain is present on the non-wicking material after a desired period, no penetration has occurred for purposes of the test. In other aspects, if at least one stain is present on the non-wicking material, penetration has occurred for purposes of the test.

In various aspects, determining the moisture permeability of the textile sample can comprise determining the amount of liquid or moisture onto the top or bottom surface of the at least one textile sample. In further aspects, the amount of liquid onto the top or bottom surface of the at least one textile sample can be determined by any desired analytical method and devices. In further aspects, the amount of liquid on the top or bottom surface of the at least one textile sample is analyzed relative to the liquid sample volume, time interval, sample size surface area, testing surface area, or a combination thereof.

A non-limiting example of the disclosed test methods can comprise:
a) Placing the bowl-shaped test specimen flat on top of a metal mesh apparatus positioned on the bottom surface of a plastic container, such that the metal mesh apparatus is capable of holding the specimen flat while testing is being conducted.
b) Slowly pour 100 ml of the stain solution through a funnel with a 10 mm (0.4 inches) spout onto the center of the bowl-shaped carpet specimen from a height of one meter (39 inches). If the carpet specimen has a fluoro-chemical finish on the face of the fiber, the following additional steps are followed:
  i. If for spillage (e.g., penetration) only, minimize the amount of movement of the specimen for 24 hours;
  ii. If the sample is being tested for spillage (e.g., penetration) and wetness, the sample should not be moved for a minimum of 3 minutes.
c) Place the sample on butcher paper on a flat surface for 24 hours undisturbed.
d) Assess the wetness and the penetration of the back of the carpet sample during at least the following time increments:
  i. 3 minutes;
  ii. 1 hour; and
  iii. 24 hours.
e) Continue assessment until the sample has reached a moisture equilibrium (dry to the touch). Record the assessment in increments of 24 hours. In operation, the staining agent can sometimes be absorbed by the fiber and no coloration appears in the backing. Therefore, in this condition, the respective 3 minute and 1 hour assessments need to be done by the touch of the hand to assess the wetness of the backing.
f) After 24 hours, assess the penetration by observing the paper for the amount of stains on the butcher paper. In this step:
  i. if only a few pin dots are present, define the number and how large the respective pin dots are;
  ii. if no stain is present on the paper, report no penetration;
  iii. if significant penetration occurs, report failure or penetration; or
  iv. if after 3 minutes or 1 hour the penetration is larger than a dime, list the sample as a failure and discontinue testing.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° F. or is at ambient temperature, and pressure is at or near atmospheric.

Example 1

The following example is an exemplary method for determining moisture permeability as disclosed herein. This exemplary procedure evaluates the moisture permeability of carpet and carpet backings to a known amount of liquid poured on the carpet face.

Sample Preparation

First, three samples can be cut in a side-center-side fashion for testing and receiving the stain solution. The three carpet samples can each be cut to a sample size of 12"×12".

Next, binder clips can be used on each corner of the carpet samples to create a bowl shape sufficient to hold a test liquid such as a stain solution.

A first exemplary stain solution test liquid can be prepared as follows:

Acid Red/Cationic Blue: 800+/−1 mg of FD&C red 40 and 2.0 g of liquid cationic blue dye or 800+/−1 mg of cationic blue dye power can be mixed in 4 liters of deionized water at 23.9+/−5.6° C. (75+/−10° F.).

Alternatively, a second exemplary stain solution test liquid can be a Methylene Blue test liquid comprised of 0.1% methylene blue aqueous solution (commercially available from Fisher). A 1.0% methylene blue solution can be diluted 1:10 for the same result.

Equipment

Large plastic container with approximate dimensions of 24" H×18" W×30" L

Metal Mesh Apparatus—capable of holding the specimen substantially level while testing is conducted.

Testing Protocol

First, the bowl-shaped test specimen can be placed flat on top of the metal mesh apparatus located on the floor of the plastic container. Next, 100 ml of the stain solution can be poured through a funnel with a 10 mm (0.4 inches) spout onto the carpet specimen from a height of one meter (39 inches). In some aspects, the stain solution can be concentrated in the center of the bowl-shaped specimen.

In some aspects, where the sample has a fluoro-chemical finish on the face of the fiber, the following steps can be included:

For determining spillage, minimize the amount of movement of the sample for 24 hours. If the sample is being tested for spillage and wetness, the sample should not be moved for a minimum of 3 minutes.

The sample can then be placed on butcher paper on a flat surface for 24 hours undisturbed.

Assessment:

Wetness and fluid penetration of the back of the sample can then be assessed during the following exemplary time increments: 3 minutes; 1 hour; and 24 hours. Because the staining agent can sometimes be absorbed by the fiber (i.e., no coloration appears in the backing), the 3 minute and 1 hour assessment preferably should be done by the touch of the hand to assess the wetness of the backing.

After 24 hours, continue assessment until the sample has reached a moisture equilibrium (dry to the touch). Record the assessment in increments of 24 hours.

After 24 hours, the fluid penetration can also be assessed by observing the paper for the amount of stains on the paper and determining the number and size of pin dot stains on the paper. In the present example, if after 3 minutes or 1 hour the penetration stain is larger than a dime, the sample can be deemed a failure and testing can be discontinued.

The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for determining moisture permeability of a textile, comprising:
    positioning at least one carpet or carpet tile textile sample in a liquid-receiving configuration, the textile sample having a top surface and an opposed bottom surface, wherein, in the liquid-receiving configuration, at least a portion of the top surface is deformed to have a concave profile that defines a testing site for receiving a predetermined amount of a liquid;
    introducing the predetermined amount of the liquid, for a predetermined period, onto the testing site defined by the top surface of the at least one textile sample; and
    determining the moisture permeability of the textile sample.

2. The method of claim 1, wherein determining the moisture permeability comprises determining the presence of any liquid on the bottom surface of the at least one textile sample.

3. The method of claim 1, wherein at least a portion of the bottom surface of the carpet or carpet tile comprises at least one backing layer.

4. The method of claim 1, wherein the testing site is defined within a center portion of the at least one textile sample, and wherein positioning the at least one textile sample in a liquid-receiving configuration comprises securing exterior portions of the at least one textile sample to maintain the at least one textile sample in the liquid-receiving configuration.

5. The method of claim 1, wherein the at least one textile sample has a fluoro-chemical finish.

6. The method of claim 5, wherein the at least one textile sample is tested for spillage, and wherein movement of the at least one textile sample is minimized for at least 24 hours.

7. The method of claim 1, wherein the moisture permeability of the textile sample is determined at least 3 minutes following introduction of the predetermined amount of liquid to the testing site.

8. The method of claim 7, wherein the presence of liquid onto the bottom surface of the at least one textile sample is determined by touching the bottom surface of the at least one textile sample.

9. The method of claim 1, wherein the moisture permeability of the textile sample is determined at least 1 hour following introduction of the predetermined amount of liquid to the testing site.

10. The method of claim 9, wherein the presence of liquid onto the bottom surface of the at least one textile sample is determined by touching the bottom surface of the at least one textile sample.

11. The method of claim 1, wherein the moisture permeability of the textile sample is determined at least 24 hours following introduction of the predetermined amount of liquid to the testing site.

12. The method of claim 11, wherein determining the permeability of the textile sample is repeated until the at least one textile sample has reached a moisture equilibrium.

13. A method for determining moisture permeability of a textile, comprising:
    positioning at least one textile sample having a fluoro-chemical finish in a liquid-receiving configuration, the textile sample having a top surface and an opposed bottom surface, wherein, in the liquid-receiving configuration, at least a portion of the top surface is deformed to have a concave profile that defines a testing site for receiving a predetermined amount of a liquid;
    introducing the predetermined amount of the liquid, for a predetermined period, onto the testing site defined by the top surface of the at least one textile sample; and
    determining the moisture permeability of the textile sample, wherein the at least one textile sample is tested for spillage and wetness, wherein movement of the at least one textile sample is minimized for at least 3 minutes, and wherein the at least one textile sample is placed onto a flat surface for at least 24 hours.

14. The method of claim 13, wherein the at least one textile sample is stationary.

15. The method of claim 13, wherein a non-wicking material is positioned between the at least one textile sample and the flat surface.

16. A method for determining moisture permeability of a textile, comprising:
  positioning at least one carpet or carpet tile textile sample in a liquid-receiving configuration, the textile sample having a top surface and an opposed bottom surface, wherein, in the liquid-receiving configuration, at least a portion of the top surface is deformed to have a concave profile that defines a testing site for receiving a predetermined amount of a liquid;
  introducing the predetermined amount of the liquid, for a predetermined period, onto the testing site defined by the top surface of the at least one textile sample; and
  determining the moisture permeability of the textile sample,
  wherein, following introduction of the predetermined amount of liquid to the testing site, the at least one textile sample is placed onto a flat surface for at least 24 hours.

17. The method of claim 16, wherein a non-wicking material is positioned between the at least one textile sample and the flat surface.

18. The method of claim 17, wherein penetration of the liquid onto the bottom surface of the at least one textile sample is determined by assessing the non-wicking material for a stain, wherein, if at least one dot of the stain is present on the non-wicking material, the number and size of the at least one dot is recorded, wherein, if no stain is present on the non-wicking material, no penetration is observed, and wherein, if at least one stain is present on the non-wicking material, penetration is observed.

* * * * *